United States Patent [19]
Villar et al.

[11] Patent Number: 6,054,286
[45] Date of Patent: Apr. 25, 2000

[54] METHODS TO IDENTIFY IMMUNOMODULATORS USING COGNATE INTERACTION OF PKC-THETA

[75] Inventors: Hugo O. Villar, Newark; John Patterson, Mountain View, both of Calif.; Anna Voronova, Wayland, Mass.; Dorit Ron; Lawrence Kauvar, both of San Francisco, Calif.; Gene Napolitano, New York, N.Y.; Nicki Vasquez, San Francisco, Calif.

[73] Assignee: Telik, Inc., South San Francisco, Calif.

[21] Appl. No.: 09/232,130

[22] Filed: Jan. 15, 1999

Related U.S. Application Data

[63] Continuation-in-part of application No. 08/665,647, Jun. 18, 1996, Pat. No. 5,935,803.

[51] Int. Cl.[7] .................................................. C12Q 1/48
[52] U.S. Cl. ............................................ 435/15; 435/975
[58] Field of Search ............................... 435/15, 7.8, 975

[56] References Cited

U.S. PATENT DOCUMENTS

| | | | |
|---|---|---|---|
| 5,283,173 | 2/1994 | Fields et al. ................................ | 435/6 |
| 5,352,660 | 10/1994 | Pawson ..................................... | 514/12 |
| 5,541,071 | 7/1996 | Kopin ...................................... | 435/7.21 |
| 5,580,979 | 12/1996 | Bachovchin ............................ | 540/504 |
| 5,582,995 | 12/1996 | Auruch et al. ............................ | 435/71 |
| 5,741,653 | 4/1998 | Kauvar et al. ........................... | 435/2.1 |
| 5,776,716 | 7/1998 | Ron et al. ................................ | 435/15 |
| 5,783,405 | 7/1998 | Mochly-Rosen et al. ................ | 435/15 |

FOREIGN PATENT DOCUMENTS

| | | |
|---|---|---|
| WO 95/21252 | 1/1995 | WIPO . |
| 97/14038 | 4/1997 | WIPO . |

OTHER PUBLICATIONS

Baier et al., J. Biol. Chem. 268: 4997–5004.
Dalrymple, M.A. et al., "The Product of the PRP4 Gene of S. cerevisiae Shows Homology of β Subunits of G Proteins," Cell 58: 811–812 (1989).
Derwent Publications Ltd., AN 94–026226 (1994).
Dynlacht, B.D. et al., "The dTAF . .80 subunit of Drosphila TFIID contains β–transducin repeats," Nature 363: 176–179 (1993).
Fong, H.K.W. et al., "Repetitive segmental structure of the transducin β subunit: Homology with the CDC4 gene and identificationof related mRNAs," Proc. Natl. Acad, Sci. USA 83: 2162–2166 (1986).
Guillemot, F. et al., "Physical linkage of a guanine nucleotide–binding protein–related gene to the chicken major histocompatibility complex," Proc. Natl. Acad. Sci. USA 86: 4594–459 (1989).
Keleher, C.A. et al., "Ssn6-Tup1 Is a General Repressor of Transcription in Yeast," Cell 68: 709–719 (1992).
Meller et al., Mol. Cell. Biol. 16: 5782–5791.
Mochly–Rosen, D. et al., "Intracellular Receptors for Activated Protein Kinase C," J. Biol. Chem 266(23): 14866–14868 (1991).

Mochly–Rosen, D. et al., "Identification of intracellular receptor proteins for activated protein kinase C," Proc. Natl Acad. Sci USA 88: 3997–4000 (1991).
Peitsch, M.C. et al., "Sequence similarity of phospholipase A2 activating protein and the G protein β–subunits: a new concept of effector protein activation in signal transduction?," TIBS 18(8): 292–293 (1993).
Penninger et al., Immunol. Rev. 135: 183–214 (1993).
Rickels et al., EMBO J. 13, 5598–5604.
Ron, D. et al., "Agonists and Antagonists of Protein Kinase C Function, Derived from its Binding Proteins" J. Biol. Chem. 269:21395–21398 (1994).
Ron, D. et al.,. "An Autoregulatory Region in Protein Kinase C: The Pseudoanchoring Site" Proc. Natl. Acad. Sci. USA 92:492–496 (1995).
Ron, D. et al., "Cloning of an Intracellular Receptor for Protein Kinase C: A Homolog of the Beta Subunit of G Proteins" Proc. Natl. Acad. Sci. USA 91:839–843 (1994).
Ruggieri, R., et al., "MSI1, a Negative Regulator of the RAS–cAMP Pathway in Saccharomyces Cerevisiae" Proc. Natl. Acad. Sci. USA 86:8778–8782 (1989).
Smith, B.L. and Mochly–Rosen, D., "Inhibition of Protein Kinase C Function by Injection of Intracellular Receptors for the Enzyme," Biochem. Biophys. Res. Comm. 188(3): 1235–1240 (1992).
Takagaki, Y. and Manley, J.L., "A Human Polyadenylation Factor Is a G Protein β–subunit Homologue," J. Biol. Chem 267(33):23471–23474.
Tamaki, M. et al. "Rat Lipocortin I cDNA" Nucleic Acids Res. 15:7637 (1987).
van der Voorn, L. and Ploegh, H.L., "The WD–40 repeat," FEBS Lett. 307(2): 131–134 (1992).
Wallner, B., et al. "Cloning and Expression of Human Lipocortin, a Phospholipase A2 Inhibitor with Potential Anti–Inflammatory Activity" Nature 320:77–81 (1986).
Weinstat–Saslow et al., "A Transducin–like Gene Maps to the Autosomal Dominant Polycystic Kidney Disease Gene Region" Genomics 18:709–711 (1993).
Williams, F.E. and Trumbly, R.J. "Characterization of TUP1, a Mediator of Glucose Repression in Saccharomyces cerevisiae, ," Mol. Cell. Biol. 10(12): 6500–6511 (1990).
Williams, F.E. et al., "The CYC8 and TUP1 Proteins Involved in Glucose Repression in Saccharomyces cerevisiae Are Associated in a Protein Complex," Mol. Cell. Biol. 11(6):3307–3316 (1991).

Primary Examiner—Charles L. Patterson, Jr.
Attorney, Agent, or Firm—Morrison & Foerster LLP

[57] ABSTRACT

Compounds having immunomodulating activity are identified using a methodology which employs TER14687, TER10311 and/or TER17210 as standards. The effect candidate compounds have on PKC-theta interaction with cognate binding proteins is measured and compared with the standards. The interaction can be measured by a variety of techniques, including assessing translocation of said PKC-theta or fragment. Kits containing the TER14687, TER10311 and/or TER17210 standards are disclosed. TER14687, TER10311 and/or TER17210 are useful in modulating the immune system in a subject by reducing T-cell activity. TER14687, TER10311, TER17210 are used as leads to develop other compounds having immunomodulating activity.

9 Claims, No Drawings

METHODS TO IDENTIFY IMMUNOMODULATORS USING COGNATE INTERACTION OF PKC-THETA

RELATION TO OTHER APPLICATIONS

This application is a continuation-in-part of Ser. No. 08/665,647 filed Jun. 6, 1996 now U.S. Pat. No. 5,975,803. The content of the foregoing applications are expressly incorporated herein by reference.

TECHNICAL FIELD

The field of this invention is methods for identifying pharmaceutical agents for use in modulating activities of the immune system, systems suitable for use in these methods, and methods of using the identified agents.

BACKGROUND ART

PCT Application WO 95/21252 discloses and claims peptide compositions which alter the activity of a signal-generating protein with respect to its cognate binding protein wherein the cognate protein contains at least one WD-40 region which putatively interacts with the signal-generating protein. The peptide compositions mimic the WD-40 regions, thus competing with the interaction of the cognate with the signal-generating protein. This competition results either in inhibiting the signal-generation or activating it.

One specifically exemplified signal-generating protein is protein kinase C (PKC); the illustrated cognate receptor for activated kinase C (RACK), in this case specific for beta-PKC, was designated RACK1. The gene encoding RACK1 was cloned and sequenced, showing that RACK1 contains the requisite WD-40 regions.

The above PCT application and U.S. Ser. Nos. 08/473,089, 08/477,346, and 08/487,072 further describe methods to identify additional pairs of signal-generating proteins and their cognates and methods for recognizing WD-40 sequences in the cognates. These applications also note that such interactions can be used as a system to identify additional molecules that bind the signal-generating protein by measuring the effect of candidate binding molecules on the interaction between the signal-generating protein and either its cognate per se or the polypeptide compositions that mimic the WD-40 regions of the cognate.

In U.S. Pat. No. 5,783,405, several specific peptides were identified that bind either to the signal-generating protein or to the cognate protein in a signal-affecting manner. The use of the signal-generating protein/cognate system to assay for modulators of signal transduction in assays which are independent of the purity of these participants was described. The PKC enzyme system was illustrated as a specific embodiment. In addition, peptides which reside on the signal-generating protein, as well as those which reside on the cognate or mimics thereof, were described as being useful to modulate the signal-generating interactions and biological activities which are mediated by the signal-generating interactions.

In U.S. Pat. No. 5,776,716, experiments that demonstrated the identity of a cognate protein for PKC-theta as the fyn protein were described. Since it is well established that fyn is involved in mediation of T-cell responses, it is apparent that disruption of the interaction of PKC-theta with its fyn cognate mediates the immune response. It is also apparent that PKC-theta is a mediator of the immune response. Substances which can be shown to disrupt the interaction between PKC-theta and its cognate fyn, or, as described hereinbelow, to influence the interaction of PKC-theta with any cognate also have immunomodulating activity. The identification of fyn as a PKC-theta cognate, and the consequences of interfering with this association, demonstrate that PKC-theta is a significant signaling protein involved in the immune response.

PCT Application WO 97/143038 and U.S. application Ser. No. 08/665,647, filed Jun. 18, 1996, both disclose an assay system for identifying modulators of the immune system. The contents of both these documents are expressly incorporated herein by reference. The assay system measures the effect of candidate substances on the interaction between a PKC-theta, or a fragment thereof, with its cognate and then compares the result obtained to that of a standard. The cognate comprises the relevant portion of a molecule which binds to PKC-theta, e.g. fyn, the fyn fragment fyn-3, the fyn fragment fyn-2, and the protein encoded by clone 2-10 or 2-32. Because the method takes advantage of inherent biological specificity, it can be conducted on impure preparations of the participants in the signal pathway—i.e., the above-mentioned signal-generating protein PKC-theta and its cognate receptor. The assay is conducted by assessing the interaction between the signal-generating protein and its cognate either by measuring binding directly or by measuring a physiological or metabolic effect. The measurement is made in the presence and in the absence of a candidate substance. Successful candidates which agonize the signal effect an increase in a metabolic or physiological output; antagonists effect a decrease. Both antagonists and agonists compete for binding between cognate and signal-generating protein. The interactions are disclosed as being measurable in a variety of ways, e.g. measuring translocation of said PKC-theta or fragment; measuring tyrosine phosphorylation of a 21 kD protein after OKT-3 stimulation of T-cells; measuring diminution of IL4 and/or IL5 production without affecting IFN production; measuring the binding of said PKC-theta or fragment to its cognate. The binding can be determined by means of a "two-hybrid" system. The contents of each of the documents described above are expressly incorporate herein by reference.

DISCLOSURE OF THE INVENTION

The present invention resides in the discovery that TER14687=2[(dimethylamino)methyl]-1-indanone (available from Sigma Aldrich Rare Chemicals, WI), TER10311=10,11-diacetoxy-10,11-dihydrdibenzo(A,D)cyclohepten-5-one (available from Sigma Aldrich Rare Chemicals) and TER17210=2[S-methylcysteinyl]-1-indanone (synthesized according to conventional synthetic methods) have immunomodulating activity. The structures for TER14687, TER10311 and TER17210 are:

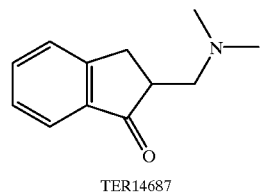

TER14687

-continued

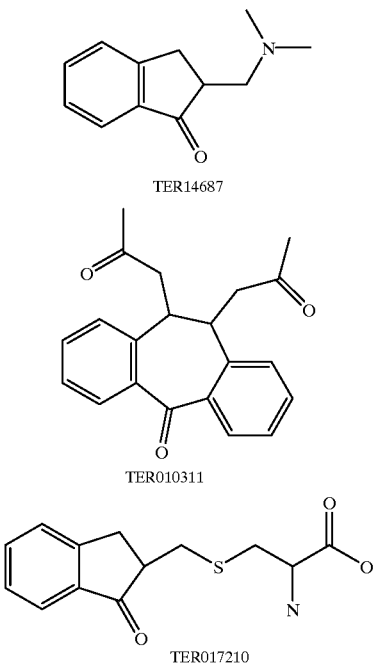

TER14687

TER010311

TER017210

An object of the invention is the use of these compounds or variants or derivatives therefrom as immunomodulating agents for the treatment of conditions such as transplant surgery, autoimmune disorders, and response to allergens.

A further object of the invention is the use of TER14687, TER10311 and TER17210 as assay standards to discover immunomodulating agents. Typical in vivo and in vitro assays where these standards may be used include those which involve the use of theta-PKC and cognates, or peptide derivatives thereof, yeast two hybrid model systems, translocation and gene transcription assays in T-cells. To facilitate handling these standards can be packaged in kit form with one or more other agents needed or associated with the practice of the screening method, e.g. PKC-theta or a fragment thereof; and a cognate of said PKC-theta. These kits can be prepared in a variety of forms, e.g. single or multiple use formats.

A still further object of the invention is the use of TER14687, TER10311 and/or TER17210 as medicinal chemistry leads. Leads can be arrived at in a variety of ways. TER14687, TER10311 and TER17210 structures can be compared in a variety of ways using a variety of means, particularly by computer modeling to identify common structural features within the molecules or to define their complementary surfaces by docking into crystal structure models of PKC/RACK. Potential lead compounds can be selected based on their meeting those common features. Likewise, compounds could be selected based on common affinity fingerprints against a small reference panel of diverse proteins as described in U.S. Pat. No. 5,741,653, the contents of which are expressly incorporated herein by reference.

In addition, variants or derivatives of TER14687, TER10311 and TER17210 can be prepared as leads by single synthesis or parallel combinatorial syntheses. These compounds can serve as leads for development using conventional techniques.

MODES OF CARRYING OUT THE INVENTION

Immunomodulating Agents Use

Interaction between PKC-theta and its cognate has been implicated in modulating a variety of biological responses. According to the present invention, TER14687, TER10311 and TER17210 are capable of modulation of the immune system, particularly those activities involving T-cell activity. Specifically, immune system activity, such as T-cell mediated responses, can be modulated by administering to a subject an effective amount of TER14687, TER10311 and TER17210. The subject can be any vertebrate in need of modulation of immune activity. These compounds or their derivatives are expected to be particularly useful in treating human subjects.

Immune system activity refers to the wide variety of cellular events in which cells of the immune system participate. TER14687, TER10311 and TER17210 can be administered to reduce T-cell activity in a subject in need of such reduction; to reduce the rate of graft rejection in a subject in need of such reduction; to reduce the severity of an autoimmune disorder in a subject in need of such reduction; to reduce the severity of rheumatoid arthritis; to ameliorate an allergic and/or asthmatic response in a subject in need of such amelioration; to diminish cytokine production in a subject in need of such diminution; to diminish IL-4 production. This can be accomplished without affecting IFN-gamma production.

TER14687, TER10311, TER17210 or their derivatives can be administered via parenteral, subcutaneous, intravenous, intramuscular, intraperitoneal, transdermal, or buccal routes. Alternatively, or concurrently, administration may be by the oral route, or by inhalation. The dosage administered will be dependent upon the age, health, and weight of the recipient, kind of concurrent treatment, if any, frequency of treatment, and the nature of the effect desired.

The present invention further provides compositions containing one or more of TER14687, TER10311, TER17210 or their derivatives. While individual needs vary, determination of optimal ranges of effective amounts of each component is within the skill of the art. Typical dosages are in the range of 0.01–50 mg/kg body weight. Preferred dosages are in the range of 0.1–10 mg/kg; most preferably 0.1–1 mg/kg.

In addition, a composition comprising TER14687, TER10311, TER17210 or their derivatives may contain suitable pharmaceutically acceptable carriers such as excipients and auxiliaries which facilitate processing of these active compounds into preparations which can be used pharmaceutically for delivery to the site of action. Suitable formulations for parenteral administration include aqueous solutions of these active compounds in water-soluble form, for example, water-soluble salts. In addition, suspensions of these active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

Suitable formulations for administration by inhalation include metered dose inhalers and dry powder devices. For nasal absorption aqueous and nonaqueous suspensions or dry powders may be used.

Immunomodulator Assay

Additionally, an assay system for identifying modulators of the immune system employs TER14687, TER10311, TER17210 or their derivatives as standards. The assay system measures the effect of candidate substances on the interaction between a signaling protein—in this case PKC-theta, or a fragment thereof, with its cognate and then compares the result obtained to that of a standard. The cognate comprises the relevant portion of a molecule which binds to PKC-theta. Because the method takes advantage of inherent biological specificity, it can be conducted on impure preparations of the participants in the signal pathway—i.e., the above-mentioned signal-generating protein PKC-theta and its cognate receptor. The assay is conducted by assessing the interaction between the signal-generating protein and its cognate either by measuring binding directly or by measuring a physiological or metabolic effect. The measurement is made in the presence and in the absence of a candidate substance. Successful candidates which agonize the signal effect an increase in a metabolic or physiological output; antagonists effect a decrease. Both antagonists and agonists compete for binding between cognate and signal-generating protein.

The general operation of the assay, with the exception of the comparison step with TER14687, TER10311, TER17210 or their derivatives as standards is described in WO 97/143038 and U.S. Pat. No. 5,935,803. The comparison step compares the measured value for the candidate compound to those obtained for one or more of the standard compounds measured under the same or similar conditions. This comparison can be with a concurrently or previously measured value of one or more of the standards. The comparison can be used to generate an index. The index can be used to define family of compounds or a library. Members of the family or library can be used to develop additional groups using combinatorial or traditional synthetic techniques.

The standards can be individually packaged in a kit form with one or more of the other reagents needed or associated with the practice of the screening method. The kits can also include multiple standards. It is also possible to include in the kit the measured values for standards in electronic or like form to facilitate comparison and standardization.

Medicinal Chemistry Leads

A still further object of the invention is the use of TER14687, TER10311 and TER17210 as medicinal chemistry leads for the development of drugs. Additional leads can be arrived at in a variety of ways. Similarities among TER14687, TER10311 and TER17210 can be found using multiple techniques. For instance, common structural features or other physicochemical properties of these molecules can be found using the methods of molecular modeling or computational chemistry. The complementarity of these molecules to the crystal structure of models of PKC/RACK, individually or interacting, can be used to identify other compounds that satisfy the identified complementarities. These compounds could differ significantly from these structures and constitute new leads on their own.

Likewise, compounds could be selected based on common affinity fingerprints. The affinity fingerprint of a compound is its distinctive pattern of binding affinity for a small reference panel of proteins, chosen based on empirically established diversity in their binding patterns to a wide assortment of small organic compounds. In this technique, identification of additional potentially active compounds is achieved by an electronic search of a database of affinity fingerprints for compounds whose fingerprints share homology with those of the standards. TER14687, for example, was selected based on fingerprint features shared with TER10311.

Other chemoinformatics tools can also be used to identify compounds that share the structure features found in common among all the compounds that display the biochemical and pharmacological activities of interest. Then, catalogs of commercially available chemicals or virtual libraries of compounds that could easily be synthesized can be searched looking for matches. Those matches can then be either synthesized or acquired, and tested.

Compounds that result from simple reactions of these chemicals could also provide new leads. Variants or derivatives can be prepared for evaluation as leads by single synthesis or by parallel combinatorial syntheses employing TER14687, TER10311 and TER17210 as scaffolds using customary combinatorial techniques. Such techniques include both liquid phase and solid phase chemistry, the latter being particularly convenient. In such procedures, a synthetic route to the final compound is established, involving coupling of substructures. Variants of each of the needed substructures can then be provided, allowing variant compounds to be produced by the same synthetic steps used to produce the original compound.

EXAMPLE 1

PKC-theta Translocation During T-cell Activation

To assess translocation, suitable cells, preferably non-transformed human T-cells, are cultured to a density of $10^6$/ml and then incubated in cytokine-free medium overnight. Ten-milliliter aliquots are used for each assay. The substance to be tested is added to the appropriate samples and incubated for 15 minutes at 37° C. Substances known to stimulate the translocation of PKC-theta are then added: typically PMA at 20–80 nM±PHA at 1 μg/ml are added, and the culture is incubated for 15 minutes at 37° C.

After the incubation period, the samples are spun at 1,000 rpm for 10 minutes and the cell pellet is washed with cold PBS. The cells are then resuspended in homogenization buffer and sonicated. They are then centrifuged at 55,000 rpm for 30 minutes to obtain a supernatant cytosolic fraction and a pellet which is resuspended in homogenization buffer with a 27-gauge needle to obtain the particulate fraction. After normalization of total protein, the content of PKC in each of the supernatant and particulate fractions is then determined using SDS-PAGE and detection using appropriate antibodies (Western blotting).

SDS-PAGE of the soluble and particulate fraction stained with anti-PKC-theta antibodies or anti-PKC-beta antibodies confirms that PKC-beta is essentially all in the soluble fraction in unstimulated cells, while PKC-theta is more or less evenly distributed between these two fractions. After stimulation with either PMA or a combination of PMA/PHA, both PKC-theta and PKC-beta are translocated to the particulate fraction. However, stimulation with OKT-3, an antibody immunoreactive with the CD3 component of T-cell receptors, which provides a more physiologically based activation, results in translocation of PKC-theta, but not PKC-beta. The ability of OKT-3 to effect, specifically, translocation of PKC-theta is evidence of the involvement of PKC-theta in transduction of T-cell receptor mediated stimulation. TER14687 inhibits the translocation of PKC-theta. This is based on experimental data obtained from a Western blot study involving subcellular distribution (Cytoplasmic vs Particulate) of PKC-theta compared to PKC-beta following T-cell stimulation by direct PKC agonists (PMA) or by the OKT3 antibody to T-cell Receptor. TER14687 inhibits the translocation of PKC-theta. If the cells were initially incubated with 20 TM of TER14687, the translocation of PKC-theta to the particulate fraction was inhibited when either OKT-3 or PMA/PHA was used as a stimulant.

The effect of TER14687 on the PKC-theta/cognate interaction can also be demonstrated by showing that TER14687 prevents tyrosine phosphorylation of a 21 kD protein after OKT-3 stimulation of T-cells, measured with an Ab to phosphotyrosine. This phosphorylation is a known downstream event of T-cell activation. TER14687 does not inhibit PKC catalytic activity in vitro, nor does it inhibit tyrosine kinase catalytic activity. Further, it does not inhibit calcium flux triggered by T-cell Receptor stimulation. The cellular effects, therefore, can be attributed to the effect on PKC-theta translocation.

EXAMPLE 2

Association of PKC-theta Activation With Allergic Reactions

A human T-cell line, TT7.5, is physiologically activated with OKT3 coated on tissue culture plates at 10 µg/ml as shown by enhanced proliferation using a tritiated thymidine assay. Activation is also characterized by enhanced secretion of interferon-gamma, and of interleukins 4 and 5, but not of IL-2, as assayed in appropriate ELISAs. This pattern characterizes a TH-2-like cell. TH-2 cells have been shown to mediate allergy via the immunoregulatory effects of IL-4 and IL-5. This pattern of cytokine production is associated with stimulation of IgE and eosinophil production and can thus be used as an in vitro model of T-cell function in mediating allergy.

In an assay that uses cytokine production as a measure of PKC-theta interaction with cognate, TER14687, administered during OKT3 activation, inhibits the production of IL-4, but not the induced production of interferon-gamma. The small decline in interferon production at high compound concentrations is likely a secondary effect of reduced number of cells consequent to absence of the IL-4 autocrine growth factor. TER14687 has preferential inhibition of proliferation and IL4 secretion in T-cells, stimulated with antibody to T-cell receptor, as compared to IFN-gamma secretion. Similar results are obtained with the TH-2-like T-cell line TT3.6. In a TH-1-type cell line (TT6.4) TER14687 inhibits OKT3-induced IL-2 production, but not interferon-gamma production. In Jurkat T-cell hybridoma cells, both TER14687 and TER10311 inhibit IL-2 production.

TER14687 also strongly inhibits expression, in TT7.5 cells, of surface markers of T-cell activation, such as CD69, CD25 and CD40L following overnight OKT3 stimulation. CD69 is expressed exclusively on activated T-cells, CD25 is a low-affinity IL-2 receptor expressed on activated T-cells and CD40L is a ligand for CD40 which is also expressed exclusively on activated T-cells. These markers were assayed using appropriately labeled fluorescent antibodies and a flow cytometer. TER14687 inhibits OKT3-induced cell surface expression of CD69, CD 25 and CD 48L in human T-cells, as measured in a FACS machine using appropriate fluorescent antibodies.

Similar results were obtained in Jurkat cells following activation by PMA rather than OKT3. In the presence of 50 µM fyn2 peptide, enhanced expression of CD69 is reduced.

EXAMPLE 3

Assay for Modulation Indexed by Binding

Recombinant PKC, produced in Baculovirus, was tested for binding to a fusion of fyn and MBP (maltose binding protein) produced in $E.$ $coli.$ The MBP-fyn fusion was spotted on nitrocellulose, and overlaid with the PKC in solution. After washing, an antibody to PKC was used to detect the captured PKC. Antibody was then quantified using a secondary antibody conjugated to HRP and appropriate substrate. TER14687 at 10 µM largely abolished binding.

The intracellular yeast two hybrid method to detect peptide/peptide binding was used a) to provide an assay system for the effect of candidate substances on interaction with PKC-theta and its cognate and b) to find additional peptides which bind to PKC-theta.

In this approach, plasmids containing the polymerase activating domain fused to fyn (or the separated kinase or regulatory domains) were mixed with yeast harboring plasmids containing PKC-theta V1 fused to the DNA binding domain. The yeast were plated onto media selecting for presence of the plasmids (THULL) plates and assayed for beta-galactosidase on filter lifts. When transformed into the parental yeast strain L40, lacking PKC-theta V1, no activation was observed by the reporter assay, nor was activation observed when theta V1 was replaced by delta V1 or an unrelated protein, lamin.

TER14687 markedly diminished binding theta V1 to fyn. As a control for toxicity to yeast or non-specific effects on the two hybrid system, TER14687 was shown not to inhibit expression of the reporter gene when the transcription factor Tal1/E2A was supplied as a two hybrid construct. TER14687 inhibits yeast two hybrid system of PKC-theta-V1 interaction with fyn, 2-10 and 2-32, as contrasted to the absence of effect of the compound on a control Tal1 interaction with E2A in the same two hybrid construct.

Using the compound TER14687 as a control, other clones have been identified which interact with the regulatory V1 domain of PKC-theta. Two such clones, 2-32 and 2-10 are illustrated in FIG. 4. Isolation of such clones from a cDNA library is described in U.S. Pat. No. 5,935,803, the contents of which are expressly incorporated herein by reference.

EXAMPLE 4

Effects of TER Compounds on Immunoglobulin Production in Balb/c Mice

BALB/c mice (6 animals per dose) were immunized by i.p. injection of alum-absorbed ovalbumin. After immunization they were given test agents for 6 consecutive days by i.p. route. The doses were 10 and 100 mg/kg per day. Ten days later, serum was taken for the measurement of IgE and anti-ovalbumin IgG antibodies. Historical data indicate that this system measures mostly TH-2 responses, and that suppression of IL-4 blocks both IgE and IgG1 in this system. Total IgE was measured, most of it being to ovalbumin. Normal IgE levels are usually 0.1 ng/ml. The IgG measured was specific to ovalbumin and most of it is thought to be IgG1. The results shown in Table 1 indicate a dose-dependent and significant inhibition of both IgE and anti-ovalbumin IgG by TER14687 and TER17210. The effects at 100 mg/kg of TER14687 and TER17210 are equivalent to the animals having been given 500 micrograms of anti-IL-4 per mouse.

TABLE 1

Effects of TER compounds on immunoglobulin production in Balb/c mice

| Compounds | Dose (mg/kg i.p.) | IgE (ng/ml serum) | % Inhibition | a-OVA IgG (ng/ml serum) | % Inhibition |
|---|---|---|---|---|---|
| Vehicle | — | 1.54 ± 0.47 | — | 94.6 ± 26.2 | — |
| TER-14687 | 10 | 1.41 ± 0.38 | 9 | 76.4 ± 18.8 | 19 |
|  | 100 | 0.87 ± 0.50 | 44 | 45.7 ± 40.2 | 42 |
| TER-17210 | 10 | 1.11 ± 0.20 | 28 | 84.1 ± 24.3 | 11 |
|  | 100 | 0.71 ± 0.23 | 54 | 48.2 ± 27.6 | 49 |

Mice were immunized intraperitoneally with OVA/alum.
Compounds were administered intraperitoneally once a day from the immunization for 6 days.
Mean ± S.C. of 6 mice.

We claim:

1. A method to identify a substance that has immunomodulating activity which method comprises
   providing an environment containing phosphokinase C-theta (PKC-theta) or a fragment thereof and a cognate of said PKC-theta under conditions wherein said PKC-theta or fragment interacts with said cognate;
   adding a candidate substance to said environment;
   determining the interaction of PKC-theta or fragment with cognate in the presence and absence of said candidate;
   comparing said interaction in presence and absence of candidate to ascertain immunomodualting activity;
   additionally comparing the immunomodulating activity of the candidate with that of a standard selected from the group consisting of TER14687, TER10311 and TER17210 to index the compound relative to one or more of these standards.

2. The method of claim 1 wherein said environment is an intracellular environment.

3. The method of claim 2 wherein determining said interaction is by measuring translocation of said PKC-theta or fragment.

4. The method of claim 2 wherein determining said interaction is by measuring tyrosine phosphorylation of a 21 kD protein after OKT-3 stimulation of T-cells.

5. The method of claim 1 wherein determining said interaction comprises determining binding of said PKC-theta or fragment to its cognate.

6. The method of claim 5 wherein said environment is an intracellular environment.

7. The method of claim 6 wherein said binding is determined by means of a reconstituted transcription factor "two-hybrid" system.

8. The method of claim 1 wherein said cognate is selected from the group consisting of fyn, the fyn fragment fyn-3, the fyn fragment fyn-2, and the protein encoded by clone 2-10 or 2-32.

9. A kit for the practice of the method of claim 1 comprising, one or more standards selected from the group consisting of TER14687, TER10311 and TER17210; PKC-theta or a fragment thereof; and a cognate of said PKC-theta, wherein the amounts of these materials are sufficient for the practice of the method.

* * * * *